US012649876B2

(12) United States Patent
Willcock et al.

(10) Patent No.: US 12,649,876 B2
(45) Date of Patent: Jun. 9, 2026

(54) HYDROGEL

(71) Applicant: LOUGHBOROUGH UNIVERSITY, Leicestershire (GB)

(72) Inventors: Helen Willcock, Leicestershire (GB); Stephen Butler, Leicestershire (GB); Marianne Rolph, Leicestershire (GB)

(73) Assignee: LOUGHBOROUGH UNIVERSITY, Leicestershire (GB)

( * ) Notice: Subject to any disclaimer, the term of this patent is extended or adjusted under 35 U.S.C. 154(b) by 735 days.

(21) Appl. No.: 17/271,383

(22) PCT Filed: Aug. 22, 2019

(86) PCT No.: PCT/GB2019/052362

§ 371 (c)(1),
(2) Date: Feb. 25, 2021

(87) PCT Pub. No.: WO2020/044022

PCT Pub. Date: Mar. 5, 2020

(65) Prior Publication Data

US 2021/0230479 A1 Jul. 29, 2021

(30) Foreign Application Priority Data

Aug. 29, 2018 (GB) ...................................... 1814015

(51) Int. Cl.

| | |
|---|---|
| ***C09K 11/02*** | (2006.01) |
| ***A61K 49/18*** | (2006.01) |
| ***C08G 83/00*** | (2006.01) |
| ***C09K 11/06*** | (2006.01) |
| ***G01N 21/64*** | (2006.01) |

(52) U.S. Cl.

CPC ........ *C09K 11/025* (2013.01); *A61K 49/1821* (2013.01); *A61K 49/1824* (2013.01); *C08G 83/003* (2013.01); *C09K 11/06* (2013.01); *G01N 21/6428* (2013.01); *C09K 2211/1044* (2013.01); *C09K 2211/182* (2013.01); *C09K 2211/185* (2013.01)

(58) Field of Classification Search

CPC .. C09K 11/025; C09K 11/06; A61K 49/1821; A61K 49/1824; C08G 83/003; G01N 21/6428

USPC ....................................................... 424/9.323

See application file for complete search history.

(56) References Cited

U.S. PATENT DOCUMENTS

| | | | |
|---|---|---|---|
| 5,280,548 | A | 1/1994 | Dickinson |
| 5,545,157 | A | 8/1996 | Van Iten |
| 5,952,236 | A | 9/1999 | Thompson et al. |
| 6,197,258 | B1 | 3/2001 | Thompson et al. |
| 6,225,127 | B1 | 5/2001 | Thompson et al. |
| 6,284,544 | B1 | 9/2001 | Thompson et al. |
| 7,807,473 | B2 | 10/2010 | Potyrailo et al. |
| 2003/0003587 | A1 | 1/2003 | Murray |
| 2005/0037512 | A1 | 2/2005 | Mohammad |
| 2008/0085566 | A1 | 4/2008 | Swager et al. |
| 2009/0130773 | A1 | 5/2009 | Ayi et al. |
| 2010/0279421 | A1 | 11/2010 | Strano |
| 2015/0362499 | A1 | 12/2015 | Chan |
| 2017/0151350 | A1 | 6/2017 | Omary |
| 2018/0223183 | A1 | 8/2018 | Riddle |

FOREIGN PATENT DOCUMENTS

| | | |
|---|---|---|
| CN | 101092423 | 12/2007 |
| CN | 101762572 | 6/2010 |
| CN | 102115570 | 7/2011 |
| CN | 105199114 | 12/2015 |
| CN | 105372421 | 3/2016 |
| CN | 105504364 | 4/2016 |
| CN | 105802610 | 5/2018 |
| JP | 2007126551 A * | 5/2007 |
| KR | 20160040883 | 4/2016 |

OTHER PUBLICATIONS

Kumar et al. J. Appl. Poly Sci. 2012, 126, 894-905. (Year: 2012).*
Sivakumar et al. J. Appl. Poly. Sci. 2002, 83, 3045-3054. (Year: 2002).*
Wang et al. Biomaterials 2010, 31, 4944-4951. (Year: 2010).*
Badugu, R. et al., 2003. A glucose sensing contact lens: A non-invasive technique for continuous physiological glucose monitoring. Journal of Fluorescence, 13(5), pp. 371-374.
Behbahani, M. et al., 2015. Application of a tailor-made polymer as a selective and sensitive colorimetric sensor for reliable detection of trace levels of uranyl ions in complex matrices. RSC Advances, 5(74), pp. 59912-59920.
Borisov, S. et al., 2008. Optical biosensors. Chemical reviews, 108(2), pp. 423-461.
Bozdemir, O. et al., 2010. Reaction-based sensing of fluoride ions using built-in triggers for intramolecular charge transfer and photoinduced electron transfer. Organic letters, 12(7), pp. 1400-1403.

(Continued)

*Primary Examiner* — Michael G. Hartley
*Assistant Examiner* — Sean R Donohue
(74) *Attorney, Agent, or Firm* — Meunier Carlin & Curfman LLC

(57) ABSTRACT

A hydrogel comprising a particle physically entrapped within a hydrogel matrix, a method for making the hydrogel, a particle for use in the hydrogel and the use of the hydrogel to sense a chemical species, especially anions in solution. The particle comprises an active material and a plurality of chains of a first polymeric material, each of the chains of the first polymeric material having a first end and a second end. The active material and the first ends of the chains form a core; and the second ends of the chains extend outwardly away from the core to form a shell. The hydrogel matrix comprises chains of a second polymeric material in the form of a three dimensional cross-linked network.

12 Claims, 7 Drawing Sheets

(56) References Cited

OTHER PUBLICATIONS

Chen, Y. et al., 2005. Role of topology and amphiphilicity for guest encapsulation in functionalized hyperbranched poly (ethylenimine) s. Macromolecules, 38(2), pp. 227-229.
Cotanda, P. et al., 2013. A comparative study of the stimuli-responsive properties of DMAEA and DMAEMA containing polymers. Journal of Polymer Science Part A: Polymer Chemistry, 51(16), pp. 3333-3338.
Esquivel-Guzmán, J. et al., 2012. Synthesis and characterization of novel polymers bearing fluorescein units: thermal and optical properties. Designed Monomers and Polymers, 15(6), pp. 561-574.
Helwa, Y. et al., 2012. Aptamer-functionalized hydrogel microparticles for fast visual detection of mercury (II) and adenosine. ACS applied materials & interfaces, 4(4), pp. 2228-2233.
Innocenzi, P. et al., 1997. Fluorescence properties of the Ru (bpy) 32+ complex incorporated in sol-gel-derived silica coating films. The Journal of Physical Chemistry B, 101(13), pp. 2285-2291.
Lowe, C., 1985. An introduction to the concepts and technology of biosensors. Biosensors, 1(1), pp. 3-16.
Pu, K.Y. et al., 2008. A multicolor cationic conjugated polymer for naked-eye detection and quantification of heparin. Macromolecules, 41(18), pp. 6636-6640.
Rounds, R. et al., 2007. Microporated PEG spheres for fluorescent analyte detection. Journal of Fluorescence, 17(1), pp. 57-63.
Russell, R. et al., 1999. A fluorescence-based glucose biosensor using concanavalin A and dextran encapsulated in a poly (ethylene glycol) hydrogel. Analytical Chemistry, 71(15), pp. 3126-3132.
Scheller, F. et al., 1985. Biosensors: trends and commercialization. Biosensors, 1(2), pp. 135-160.
Shibata, H. et al., 2010. Injectable hydrogel microbeads for fluorescence-based in vivo continuous glucose monitoring. Proceedings of the National Academy of Sciences, 107(42), pp. 17894-17898.
Turner, A. et al., 1987. Biosensors: fundamentals and applications. Oxford university press, pp. 85-92 and 617-637.
Vilozny, B. et al., 2011. Multiwell plates loaded with fluorescent hydrogel sensors for measuring pH and glucose concentration. Journal of Materials Chemistry, 21(21), pp. 7589-7595.
Wang, B.Y. et al., 2009. Synthesis and photophysical behavior of a water-soluble coumarin-bearing polymer for proton and Ni2+ ion sensing. Polymer international, 58(6), pp. 703-709.
Wang, J., 2001. Glucose biosensors: 40 years of advances and challenges. Electroanalysis: An International Journal Devoted to Fundamental and Practical Aspects of Electroanalysis, 13(12), pp. 983-988.
Wu, S. et al., 2018. Hydrogel-Based Fluorescent Dual pH and Oxygen Sensors Loaded in 96-Well Plates for High-Throughput Cell Metabolism Studies, Sensors (Basel), 18(2):564.
Yang, C. et al., 2013. An efficient Eu-based anion-selective chemosensor: Synthesis, sensing properties, and its use for the fabrication of fluorescent hydrogel probe. Sensors and Actuators B: Chemical, 177, pp. 437-444.
Zhang, C. et al., 2013. Hydrogel-based glucose sensors: effects of phenylboronic acid chemical structure on response. Chemistry of Materials, 25(15), pp. 3239-3250.
The Molecular Probes Handbook. A Guide to Fluorescent Probes and Labeling Technologies, 11th Edition (2010), Thermo Fisher Scientific, pp. 66-69.
International Search Report and Written Opinion in PCT/GB2019/052362. Mailed Oct. 28, 2019. 12 pages.
GB Search report in GB1814015.2. Mailed Mar. 15, 2019. 5 pages.
Polymer Chemistry, vol. 7, 2016, A B Mabire et al., CO2/pH responsive particles with built-in fluorescence read-out, pp. 5943-5948.
Butler (2015)—Chem. Commun., 2015, 51, 10879.
Butler (2017)—Chem. Commun., 2017, 53, 12626.

* cited by examiner

123

HYDROGEL

CROSS REFERENCE TO RELATED APPLICATIONS

This application is a United States National Phase Patent Application of International Patent Application Number PCT/GB2019/052362, filed on Aug. 22, 2019, which claims the benefit of priority to GB Application No. 1814015.2, filed Aug. 29, 2018, which is incorporated by reference herein in its entirety.

A hydrogel, a method for the preparation of a hydrogel, and the use thereof.

The ability to continually monitor ions in solution would be of significant benefit to many fields. For example, monitoring of anions, such as phosphate and fluoride, in water supplies to ensure safe levels are obtained. Monitoring of blood content for different ions could impact on both intensive care and condition management.

Sensors have been reported that involve immobilisation of the sensor through attachment to a surface, or entrapment within, polymeric materials, or through direct polymerisation into the polymer backbone. However, a major obstacle that must be overcome is the ability to immobilise sensors in, or onto, polymeric substrates without having a detrimental impact on the sensing ability of the overall material. One approach to immobilising sensors involves covalent attachment of a colorimetric or luminescent molecule to a polymeric scaffold. However, this process requires additional synthesis of sensors with a suitable point of chemical attachment, which can adversely affect its sensing properties.

Problems with immobilisation can manifest as diminished sensing ability, including through incompatibility between the sensor and the material, diffusion, and leaching of the sensor from within the material.

Immobilisation also results in problems with a lack of reusability for the sensors, and irreversible reaction of the sensor with the target ion/molecule. It is a combination of impact on sensing ability, limited reusability, and the desire to monitor solution based ions that has limited the development of polymer immobilised sensors, with no currently reported versatile and facile method for immobilising a range of sensors onto, or within, a stable polymeric scaffold for solution based real-time monitoring of ions.

According to a first aspect of the invention there is provided a hydrogel comprising a particle physically entrapped within a hydrogel matrix;

- the particle comprising an active material and a plurality of chains of a first polymeric material, each of the chains of the first polymeric material having a first end and a second end;
- wherein the active material and the first ends of the chains form a core and the second ends of the chains extend outwardly away from the core to form a shell; and
- the hydrogel matrix comprises a second polymeric material in the form of a three dimensional cross-linked network.

Active materials include luminescent dyes, luminescent sensors, MRI contrast agents, catalysts (e.g. organocatalysts and catalysts based on metal complexes), and pharmaceuticals (including small molecule drugs such anticancer drugs, e.g. cisplatin).

The active material may be a luminescent material. Hence the invention also resides in a luminescent hydrogel comprising a particle physically entrapped within a hydrogel matrix;

- the particle comprising a luminescent material and a plurality of chains of a first polymeric material, each of the chains of the first polymeric material having a first end and a second end;
- wherein the luminescent material and the first ends of the chains form a core and the second ends of the chains extend outwardly away from the core to form a shell; and
- the hydrogel matrix comprises a second polymeric material in the form of a three dimensional cross-linked network.

The active material may be a metal complex (luminescent or otherwise). Hence the invention also resides in a hydrogel comprising a particle physically entrapped within a hydrogel matrix;

- the particle comprising a metal complex and a plurality of chains of a first polymeric material, each of the chains of the first polymeric material having a first end and a second end;
- wherein the metal complex and the first ends of the chains form a core and the second ends of the chains extend outwardly away from the core to form a shell; and
- the hydrogel matrix comprises a second polymeric material in the form of a three dimensional cross-linked network.

According to a second aspect of the invention there is provided a method for the preparation of the hydrogel of the first aspect, the method comprising

- providing a particle comprising an active material and a plurality of chains of a first polymeric material, each of the chains of the first polymeric material having a first end and a second end; the active material and the first ends of the chains forming a core and the second ends of the chains extending outwardly away from the core to form a shell; and
- cross-linking chains of a second polymeric material in the presence of the particle to produce a hydrogel matrix having the particle entrapped therein.

The active material may be a luminescent material. Hence the invention also resides in a method for the preparation of the luminescent hydrogel, the method comprising

- providing a particle comprising a luminescent material and a plurality of chains of a first polymeric material, each of the chains of the first polymeric material having a first end and a second end; the luminescent material and the first ends of the chains forming a core and the second ends of the chains extending outwardly away from the core to form a shell; and
- cross-linking chains of a second polymeric material in the presence of the particle to produce a hydrogel matrix having the particle entrapped therein.

The active material may be a metal complex (luminescent or otherwise). Hence the invention also resides in a method comprising

- providing a particle comprising a metal complex and a plurality of chains of a first polymeric material, each of the chains of the first polymeric material having a first end and a second end; the metal complex and the first ends of the chains forming a core and the second ends of the chains extending outwardly away from the core to form a shell; and
- cross-linking chains of a second polymeric material in the presence of the particle to produce a hydrogel matrix having the particle entrapped therein.

The invention resides in the combination of engaging the active material (e.g. luminescent material) with the first polymeric material to form the particles and subsequently (physically) trapping the particles within a hydrogel i.e. "secondary encapsulation". The two step method leads to a decrease in leaching of the active material from the hydrogel, as compared to when the material is not part of the particles. Without being bound by theory we submit that the hydrogel matrix sterically hinders leaching of particles.

The method of the invention has broad applications. A wide range of active materials and hydrogels can be employed. It will be understood that the particles are physically entrapped in the hydrogel matrix rather than chemically bonded to the matrix. This entrapment method enables a variety of active materials (e.g. different molecular sensors) to be immobilised readily, without chemical modification of the sensor which is beneficial economically and environmentally. Synthetic modification of sensors often requires the use of hazardous chemicals and solvents. The invention eliminates this need. In addition, it allows for a straightforward preparation without the need for complex synthetic and purification steps associated with covalent bonding.

It will be understood that the active material and the chains of polymeric material are preferably separate entities. There is no need for the active material to chemically react with the polymer chains to form the particle. The use of separate entities provides a flexible system where a range of active materials can be easily incorporated into particles (primary encapsulation) and into the hydrogel (secondary encapsulation). The active material remains stable and well defined, thereby maintaining its properties despite encapsulation. For example, where the active material is a metal complex, the sensor may remain well defined and kinetically stable and thereby able to function consistently, e.g. for diagnosis of a medical condition.

Referring to FIG. 1A there is shown a schematic representation of a particle 10 in accordance with an embodiment of the invention. The particle comprises active material 12 and a plurality of chains 14 of a first polymeric material. Each chain has two opposite ends. One end interacts with the active material 12 to form a core portion and the rest of the chain extends outwardly from the core to form a shell. The particles can be considered to be "stars": having tails/arms extending away from the core. FIG. 1B is a schematic representation of how the particles 10 are trapped within the hydrogel matrix. Polymeric chains 16 of the second polymeric material (illustrated as wavy lines) are tangled together to form a three dimensional matrix or network and the particles 10 are physically trapped within the matrix.

The structure of the particles is especially useful for sensing anions in solution. The active material is encapsulated, and does not leach from the hydrogel. However, anions can still access the active material by moving through the polymer chains to reach the core. The particles can be described as porous and tunable particles.

CN105199114 describes a synthesis of a photoluminescent europium-containing polymer hydrogel material. The method comprises the following steps: carrying out binary copolymerization on an alkene double bond-containing europium-containing active complex monomer and vinyl acetate to prepare a europium-containing polymer; hydrolyzing the polymer to obtain polyvinyl alcohol; and dissolving the polyvinyl alcohol in water; and repeatedly freezing and thawing to obtain the luminescent hydrogel material.

The present invention differs from CN105199114 in requiring the luminescent material to be physically trapped within a hydrogel matrix. Moreover, the present invention requires the luminescent material to be part of a particle. In contrast the CN105199114 method requires the europium complex to be covalently bonded to a polymer, which subsequently forms the hydrogel and does not employ particles.

CN105802610 describes a fluorine-ion fluorescent probe that is loaded into a nanometre hydrogel. The CN10502610 method does not entrap the particles within a hydrogel matrix. Instead these water dispersed particles are used in the context of cellular imaging, which requires water solubility. In contrast our technology creates a solid hydrogel material.

WO2007050463 describes a hydrogel sensor film comprising a quaternary ammonium, quaternary phosphonium, quaternary imidazolium, quaternary pyridium, quaternary pyrrolidinium, or quaternary sulfonium salt, and an indicator, dye, pigment or reagent and/or its combinations. This technique relies on ion-ion interactions between the gel and the sensing molecule.

EP1510817A1 describes microencapsulated oxygen-sensing particles (MOSPs). The MOSPs consist of a core comprising at least one oxygen-sensing particle (e.g. ruthenium dye-adsorbed silica gel particles); and a hydrophobic coating material (e.g. silicone rubber) surrounding the core. The MOSPs may be incorporated into a three-dimensional hydrogel matrix. It will be understood that MOSPs are very different from the particles of the present invention and do not offer the same benefits in relation to anion sensing.

US2008/085566A1 relates to an application of Forster resonance energy transfer (FRET), which is a mechanism describing energy transfer between two light-sensitive molecules (chromophores). The examples employ europium doped polystyrene particles coated with a luminescent polymer. The particles may be suspended in a hydrogel matrix. It will be understood that the particles of the present invention are very different from those described in US2008/085566A1 and do not offer the same benefits in relation to anion sensing.

JP2007126551A describes a fine particle of a fluorescent resin that contains a polymer particle having a hydrophobic core and a hydrophilic shell structure. The hydrophobic core contains a polymer having a functional group for coordinating a lanthanoid cation. The polymer coordinates directly to a lanthanioid cation, so they are not separate entities.

Particle

The particle comprises a core portion and a shell portion. The first "inner" ends of the chains of the first polymeric material cluster around the active material to form the core and second "outer" ends extend away to form the shell portion or "corona" around the core. The polymeric chains may have differing lengths and may be produced from the same or different monomers.

The size of the particles in solution can be determined using dynamic light scattering (DLS). DLS essentially measures fluctuations in scattered light intensity due to diffusing particles. The particle may have a diameter of 50 to 1000 nm (e.g. 50 to 500 nm or 100 to 300 nm) when measured in solution (e.g. by DLS).

It will be appreciated that the particles of the present invention are much smaller than polystyrene/silica beads, which have been used to adsorb luminescent dyes. While hydrogels have been described as support materials for such larger luminescent particles, the skilled person would not contemplate physically entrapping the particles of the present application.

Particle size can be measured by DLS by diluting a sample of an aqueous solution of the particles (e.g. after purification) with water (e.g. deionised water) until the sample is no longer opaque. A low concentration (e.g. 1 mg/mL or lower) is desirable to obtain a good signal. A drop of salt solution can be added to prevent particle interactions.

Providing the particle may comprise providing an aqueous solution/suspension of the particles, i.e. the isolated particles.

The first polymeric material comprises at least one co-polymer formed from two or more monomers.

At least one monomer may be a (meth) acrylate monomer, e.g. a monomer having the general structure $H_2C{=}CR{-}C({=}O){-}OR^1$ where R is H or $CH_3$ and $R^1$ is an organic group. The first polymeric material may comprise a co-polymer formed from two or more (meth) acrylate monomers, such as two or more methacrylate monomers (R is $CH_3$).

The first polymeric material may be formed from at least one (meth) acrylate monomer wherein $R^1$ is an organic group having a total of from 1 to 12 carbon atoms, such as from 1 to 6 carbon atoms. This includes HEMA, DEAEMA and MMA, and some PEGMA.

$R^1$ may include moieties selected from: alkyl, heteroalkyl, alkenyl, carbonyl, ether, ester, phenyl, cycloalkyl, cycloalkenyl and heterocycloalkyl moieties.

It will be understood that one such moiety may by itself form the organic group $R^1$, (for example, the organic group $R^1$ may be solely made up of an alkyl or cycloalkyl moiety), or that two or more such moieties may be combined to form the organic group $R^1$ (for example, the organic group $R^1$ may be made up of an alkyl moiety and a phenyl moiety, or a cycloalkyl moiety and an alkyl moiety). There may be two or more of the same type of moiety present within the organic group.

In one embodiment $R^1$ comprises or consists of an alkyl moiety or a heteroalkyl moiety, wherein the heteroatom is O or N.

The alkyl moieties are preferably C1-C12 moieties, such as C1-C4 moieties (methyl, ethyl, propyl or butyl). The alkenyl moieties are preferably C2-C12 moieties, such as C2-C4 moieties. The cycloalkyl moieties are preferably C5-C12 moieties, such as C5 to C6 moieties. The cycloalkenyl moieties are preferably C5-C12 moieties. The heterocycloalkyl moieties are preferably C5-C12 moieties.

Some or all of the monomers used to form the first polymeric material may be (meth)acrylate monomers. In embodiments, 70 wt % or more, such as 75 wt % or more, 80 wt % or more, 85 wt % or more, or 90 wt % or more, or 95 wt % or more, or 99 wt % or more, of the monomers used to form the first polymeric material are (meth) acrylate monomers (e.g. HEMA and/or PEGMA).

The first polymeric material may be formed from a monomer having a number-average molecular weight ($M_n$ g/mol) of at least 100, 200, 300, 400 or 500 and/or no more than 1000, 800, 600, 500, 300 or 200, e.g. an $M_n$ of from 200 to 500.

The first polymeric material may be formed from a monomer having a weight-average molecular weight ($M_w$ g/mol) of at least 100, 200, 300, 400 or 500 and/or no more than 1000, 800, 600, 500, 300 or 200, e.g. an $M_w$ of from 200 to 500.

Examples of (meth) acrylate monomers for use in the preparation of the particles are provided below.

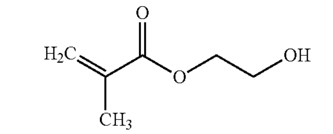

2-hydroxyethyl methacrylate (HEMA, CAS 868-77-9)
R is $CH_3$ and $R^1$ is $CH_2CH_2OH$

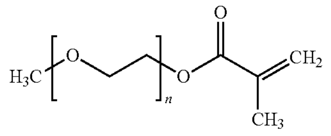

Poly(ethylene glycol) methyl ether methacrylate (PEGMA, CAS 26915-72-0)
R is $CH_3$ and $R^1$ is $(CH_2CH_2O)_nCH_3$

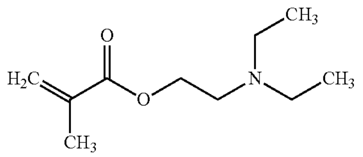

2-(diethylamino) ethyl methacrylate (DEAEMA, CAS105-16-8)
R is $CH_3$ and $R^1$ is $CH_2CH_2N(CH_2CH_3)_2$

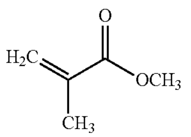

methyl methacrylate (MMA, CAS 80-60-6)
R is $CH_3$ and $R^1$ is $CH_3$ butyl methacrylate (CAS 97-88-1)
R is $CH_3$ and $R^1$ is $CH_3$ is $CH_2CH_2CH_2CH_3$ glycidyl methacrylate (2,3-epoxypropyl methacrylate, CAS 106-91-2)
R is $CH_3$ and $R^1$ is $CH_2CHCH_2O$ -continued

| | |
|---|---|
| 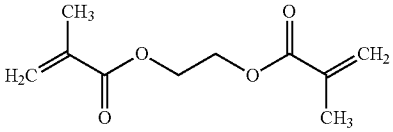 | ethylene glycol dimethacrylate (EGDMA, CAS 97-90-5) |

The first polymeric material may be formed from a HEMA monomer. The HEMA monomer can be cross-linked with a difunctional vinylic monomer, for example EGDMA The first polymeric material may be formed from a PEGMA monomer. The PEGMA monomer can be cross-linked with a difunctional vinylic monomer, for example EGDMA.

The PEGMA monomer may have a $M_n$ of at least 200, at least 300, at least 500, at least 900, at least 1500 or at least 4000 and/or no more than 5000, no more than 2000, no more than 1000 or no more than 500. The PEGMA monomer may have a $M_n$ of at least 200 and no more than 500.

The first polymeric material may be formed by co-polymerising an "inner" monomer and an "outer" monomer. The terms "inner" and "outer" relates to the location in the resulting particle. The "inner" monomer may be selected to provide the first end of the polymer chain and the "outer" monomer may be selected to provide the second end of the polymer chain. Suitable "inner" monomers include (meth) acrylate monomers, such as DEAEMA (pH responsive) and methyl methacrylate (non-responsive to pH).

Suitable "outer" monomers include (meth) acrylate monomers, such HEMA, PEGMA, butyl methacrylate and glycidyl methacrylate.

Suitable cross-linkers for the "inner" and "outer" monomers include ethylene glycol dimethacrylate (EGDMA, CAS97-90-5).

Preparation of the Particle(s)

The method may employ an initial step of preparing the particle(s). This step is separate from the subsequent cross-linking of the chains of the second polymer. The particle may be prepared by co-polymerising at least two monomers in the presence of the active material.

The active material may be engaged to the polymeric chains by physical interactions only. For example, where the active material is a metal complex, it can be engaged with the polymeric chains due to hydrophobic/hydrophilic interactions. Preferably, the active material is not covalently attached to the polymeric chains.

Preparation of the particle(s) may comprise purification of the particle(s), e.g. by dialysis or precipitation.

Entrapping the Particle(s) within a Hydrogel Matrix

The hydrogel matrix comprises a second polymeric material in the form of a three dimensional cross-linked network. Hydrogels are highly hydrophilic, three dimensionally cross-linked polymer networks. They swell in water (e.g. up to 99% w/w), without dissolution of the polymer matrix.

Entrapping the particles within the hydrogel matrix comprises forming a hydrogel matrix in the presence of the particles, i.e. cross-linking polymer chains to form a hydrogel matrix thereby trapping the particles within.

The hydrogel matrix should be sufficiently permeable to allow for small molecules and ions to penetrate and interact with the particles that are immobilised therein. For luminescent materials, this will result in a measurable luminescent response. However the materials should be sufficiently stable to prevent significant leaching of the particles.

Hydrogels can be divided into two categories depending on the nature of the crosslinking: chemically cross-linked hydrogels and physically cross-linked hydrogels. Physically cross-linked hydrogels are formed through non-covalent interactions, for example hydrophobic interactions, and hydrogen bonding, whilst chemically cross-linked hydrogels are formed as a consequence of covalent cross-linking of polymer chains through, for example, polymerization of difunctional monomers.

Entrapping the particles within the hydrogel matrix may comprise chemically cross-linking polymer chains in the presence of the particles, e.g. covalently bonding the polymer chains in the presence of the particles. In particular, cross-linking may be achieved by polymerization of difunctional monomers (e.g. EGDMA). Chemically cross-linking may be achieved by photopolymerization, enzymatic cross-linking or condensation/addition, for example.

Entrapping the particles within the hydrogel matrix may comprise mixing the particles with a hydrogel precursor to form a mixture. The hydrogel precursor may comprise monomers (e.g. (meth)acrylate monomers) and a radical initiator. Azobisisobutyronitrile (AIBN) and/or potassium persulphate may be employed as a radical initiator. The hydrogel precursor may comprise a difunctional monomer to serve as a cross-linker, e.g. a dimethacrylate, such as EGDMA, MBAc, PEGDMA. The hydrogel precursor may comprise at least 5 wt %, at least 10 wt % or at least 20 wt % difunctional monomer and/or no more than 80 wt %, no more than 50 wt %, or no more than 30 wt % difunctional monomer (such as dimethacrylate).

The mixture may be placed in a mould (e.g. a silicone mould). The mixture may be cured (e.g. in an oven) to form the hydrogel.

The second polymeric material comprises a co-polymer formed from two or more monomers. At least one monomer may be a (meth) acrylate monomer, e.g. a monomer having the general structure $H_2C{=}CR{-}C({=}O){-}OR^1$ where R is H or $CH_3$ and $R^1$ is an organic group. The second polymeric material may comprise a co-polymer formed from two or more (meth)acrylate monomers.

The second polymeric material may be formed from at least one (meth)acrylate monomer wherein $R^1$ is an organic group having a total of from 1 to 12 carbon atoms, such as from 1 to 6 carbon atoms.

$R^1$ may include moieties selected from: alkyl, heteroalkyl, alkenyl, carbonyl, ether, ester, phenyl, cycloalkyl, cycloalkenyl and heterocycloalkyl moieties, It will be understood that one such moiety may by itself form the organic group $R^1$, (for example, the organic group $R^1$ may be solely made up of an alkyl or cycloalkyl moiety), or that two or more such moieties may be combined to form the organic group $R^1$ (for example, the organic group $R^1$ may be made up of an alkyl moiety and a phenyl moiety, or a cycloalkyl moiety and an alkyl moiety). There may be two or more of the same type of moiety present within the organic group.

$R^1$ may comprise or consist of an alkyl moiety, optionally substituted with O or N.

The alkyl moieties are preferably C1-C12 moieties, such as C1-C4 moieties (methyl, ethyl, propyl or butyl). The alkenyl moieties are preferably C2-C12 moieties, such as C2-C4 moieties. The cycloalkyl moieties are preferably C5-C12 moieties, such as C5 to C6 moieties. The cycloalkenyl moieties are preferably C5-C12 moieties. The heterocycloalkyl moieties are preferably C5-C12 moieties.

Some or all of the monomers used to form the second polymeric material may be (meth)acrylate monomers. In embodiments, 70 wt % or more, such as 75 wt % or more, 80 wt % or more, 85 wt % or more, or 90 wt % or more, or 95 wt % or more, or 99 wt % or more, of the monomers used to form the second polymeric material are (meth) acrylate monomers (e.g. HEMA and/or PEGMA).

The second polymeric material may be formed from a monomer having a number-average molecular weight ($M_n$ g/mol) of at least 100, 200, 300, 400 or 500 and/or no more than 1000, 800, 600, 500, 300 or 200, e.g. an $M_n$ of from 200 to 500.

The second polymeric material may be formed from a monomer having a weight-average molecular weight ($M_w$ g/mol) of at least 100, 200, 300, 400 or 500 and/or no more than 1000, 800, 600, 500, 300 or 200, e.g. an $M_w$ of from 200 to 500.

Examples of (meth) acrylate monomers for use in the preparation of the hydrogel matrix are provided below.

In one embodiment the active material is a luminescent material and/or a metal complex.

A luminescent material emits light (without combustion or perceptible heat). Luminescence includes phosphorescence, fluorescence, and bioluminescence.

The use of a luminescent material (e.g. luminescent dye or sensor) yields a luminescent hydrogel. The luminescent hydrogel may constitute a sensor, whereby the luminescence response depends on the environment i.e. stimuli. In particular, the luminescent material may sense ions (cations or anions). The luminescent material may sense ions such as fluoride (an anion) or sodium (a cation), e.g. by binding reversibly to a target ion. The luminescent material may bind reversibly to nucleoside polyphosphate (NPP) anions, such as ATP, ADP, GTP and GDP. The inventors propose the measurement of NPP anions to diagnose a medical condition, such as stroke or TIA.

The luminescent material may comprise a metal complex, such as a cationic metal complex. The metal complex may comprise a metal selected from one or more of: Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Eu, Tb, Gd and Yb.

The metal complex may comprise a metal selected from copper, ruthenium, zinc, and iridium.

The metal complex may comprise a metal selected from the lanthanide ions, such as europium, terbium, gadolinium and ytterbium.

| | |
|---|---|
| 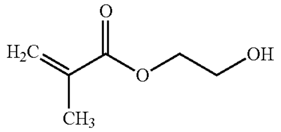 | 2-hydroxyethyl methacrylate (HEMA, CAS 868-77-9)<br>R is $CH_3$ and $R^1$ is $CH_2CH_2OH$ |
| 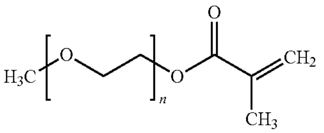 | Poly(ethylene glycol) methyl ether methacrylate (PEGMA, CAS 26915-72-0)<br>R is $CH_3$ and $R^1$ is $(CH_2CH_2O)_nCH_3$ |
| 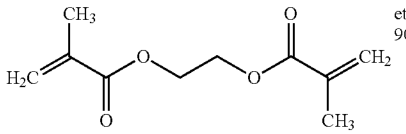 | ethylene glycol dimethacrylate (EGDMA, CAS 97-90-5) |

The second polymeric material may comprise a p(HEMA-co-EGDMA) hydrogel, a p(PEGMA-co-EGDMA) hydrogel, and/or a p(HEMA-co-polyethylene glycol-co-EGDMA) hydrogel.

The hydrogel may be an alginate hydrogel, such as an ionically cross-linked hydrogel, e.g, calcium alginate.

The hydrogel may be a polyacrylamide hydrogel, such as a poly-(N,N-dimethyl acrylamide) (PDMA) hydrogel. The hydrogel may be a clay cross-linked PDMA.

Active Material

The active material provides properties to the hydrogel and can be considered to be a functional component. The hydrogel can be used to deliver the active materials and/or as a sensor.

Active materials include luminescent dyes, luminescent sensors, MRI contrast agents, catalysts (e.g. organocatalysts and catalysts based on metal complexes), and pharmaceuticals (e.g. small molecule drugs such anticancer drugs such as cisplatin).

The metal complex may comprise a europium complex, such as a Eu(III) complex, such as:

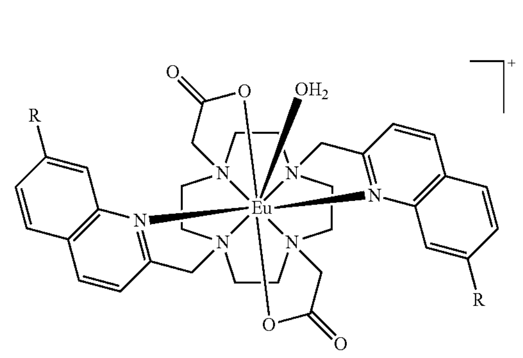

wherein each R may be independently selected from hydrogen, C1-C12 alkyl, or $NHCOR^1$, where $R^1$ is H or C1-C12 alkyl.

The C1-C12 alkyl moieties may be C1-C8 moieties, such as C1-C4 moieties (methyl, ethyl, propyl or butyl).

The metal complex may comprise a europium complex ($[Eu.L^1]^+$ or $[Eu.L^2]^+$) as previously disclosed by the inventor (Chem. Commun., 2015, 51, 10879):

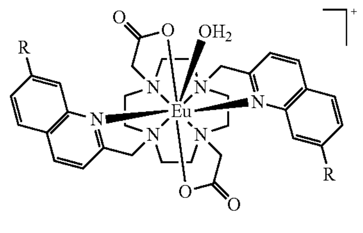

$[Eu.L^1]^+$ (R = NHCOMe)
$[Eu.L^2]^+$ (R = H)

These metal complexes are useful for rapid detection of fluoride in water.

The metal complex may comprise a europium complex ($[Eu.L^1]^+$ as previously disclosed by the inventor (Chem. Commun., 2017, 53, 12626; Chem. Sci., 2019, 10, 5373-5381):

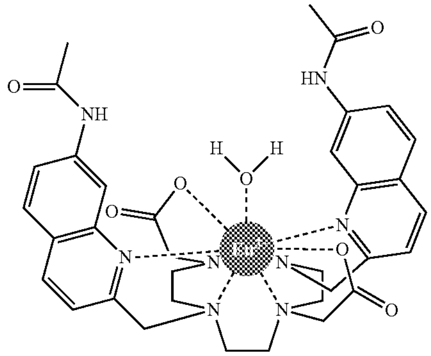

$[Eu.1]^+$

This stable cationic europium complex provides a luminescence assay for kinase activity by binding reversibly to ATP and ADP in water, at neutral pH, in the presence of $Mg^{2+}$ ions.

The metal complex may be a ruthenium complex, such as a Ru(II) complex. The ruthenium complex may be tris(2,2'-bipyridyl)dichlororuthenium (II) hexahydrate ($Ru(bpy)_3$))

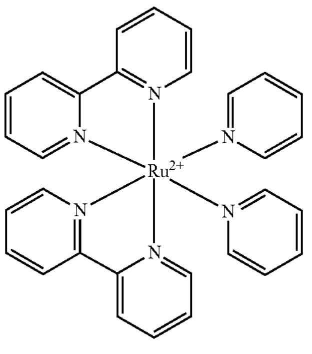

$2Cl^-$
$\cdot 6H_2O$

The luminescent material may be an organic molecule. The luminescent material may be a fluorescent protein (e.g. green, yellow or red fluorescent proteins) or a non-protein fluorophore. A non-protein fluorophore is preferred due to the large size of the proteins.

Non-protein organic fluorophores include xanthene derivatives (fluorescein, rhodamine, Oregon green, eosin, and Texas red); cyanine derivatives (cyanine, indocarbocyanine, oxacarbocyanine, thiacarbocyanine, and merocyanine); squaraine derivatives and ring-substituted squaraines (including Seta, SeTau, and Square dyes); naphthalene derivatives (dansyl and prodan derivatives); coumarin derivatives; oxadiazole derivatives (pyridyloxazole, nitrobenzoxadiazole and benzoxadiazole); anthracene derivatives (anthraquinones, including DRAQ5, DRAQ7 and CyTRAK Orange); pyrene derivatives (cascade blue, etc); oxazine derivatives (Nile red, Nile blue, cresyl violet, oxazine 170, etc); acridine derivatives (proflavin, acridine orange, acridine yellow, etc.); arylmethine derivatives (auramine, crystal violet, malachite green); and tetrapyrrole derivatives (porphin, phthalocyanine, bilirubin)

The luminescent material may be a xanthene derivative, such as fluorescein or a derivative thereof. The sodium salt of fluorescein has the structure:

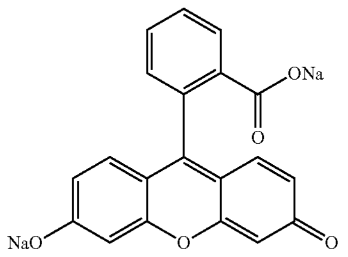

The luminescent material may be Sodium Green™ (available from ThermoFisher).

The active material may comprise a metal complex: a metal ion coordinated by ligands. The metal complex may be luminescent metal complex, as discussed above, but this is not essential.

The metal complex may comprise a metal selected from one or more of: Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Eu, Tb, Gd and Yb.

The metal complex may be a catalyst. Catalysts change the rate of a reaction, but do not alter the position of equilibrium.

The metal complex may be an MRI contrast agent, a contrast agents used to improve the visibility of internal body structures in magnetic resonance imaging (MRI). For example, the metal complex may be a gadolinium-containing contrast agent.

The metal complex may be a pharmaceutical, such as a chemotherapy medication, e.g. cisplatin.

Hydrogel

The hydrogel (e.g. luminescent hydrogel) comprises a first polymeric material (that forms the particle together with the active material) and a second polymeric material (that forms the hydrogel matrix). It will be understood that the first and second polymeric materials may be the same or different.

For example, each of the first polymeric material and the second polymeric material may be a co-polymer that is formed from at least two monomers wherein at least one monomer comprises HEMA.

According to a third aspect of the invention there is provided a particle comprising a luminescent material and a plurality of chains of a first polymeric material, each chain of the first polymeric material having a first end and second end, wherein the luminescent material and the first ends of the chains form a core and the second ends of the chains extend outwardly away from the core to form a shell.

The particle is as described above. In one embodiment the active material is a luminescent material that comprises a metal complex, such as a cationic metal complex.

The metal complex may be a europium complex, such as a Eu(III) complex. The metal complex may comprise a europium complex ($[Eu.L^1]^+$ or $[Eu.L^2]^+$) as previously disclosed by the inventor (Chem. Commun., 2015, 51, 10879):

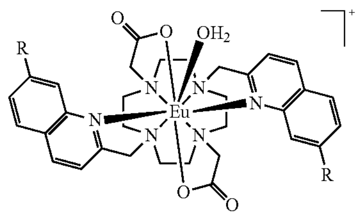

$[Eu.L^1]^+$ (R = NHCOMe)
$[Eu.L^2]^+$ (R = H)

According to a fourth aspect of the invention there is provided a method for measuring the concentration of a chemical species in a sample, the method comprising contracting the sample with the luminescent hydrogel of the first aspect;

measuring a change in an optical property of the luminescent material produced by contacting the sample with the luminescent material; and converting said change in optical property to said concentration.

The optical response may be in the UV, visible, or near-IR spectral ranges. The change in optical property may comprise a change in elastic scattering, inelastic scattering, absorption, luminescence intensity, luminescence lifetime or polarization state.

The method allows continuous monitoring of the concentration of the chemical species in the sample. The chemical species may be an ion, such as an anion (negatively charged ion) or a cation (positively charged ion). For example, the chemical species may be a nucleoside polyphosphate (NPP) anion, such as ATP, ADP, GTP and GDP.

The sample may be a fluid sample, such as an aqueous sample.

The sample may be a biological fluid, such as a blood sample or a urine sample. The method is typically carried out in vitro rather than in vivo.

The method may be employed to assist in diagnosing a medical condition. In particular, the inventors propose the use of the method to diagnose a stroke and/or a transient ischemic attack (TIA). Both are caused by a disruption in blood flow to the brain, or cerebral blood flow (CBF).

Embodiments of the invention will now be described with reference to the following figures.

Figure 4:
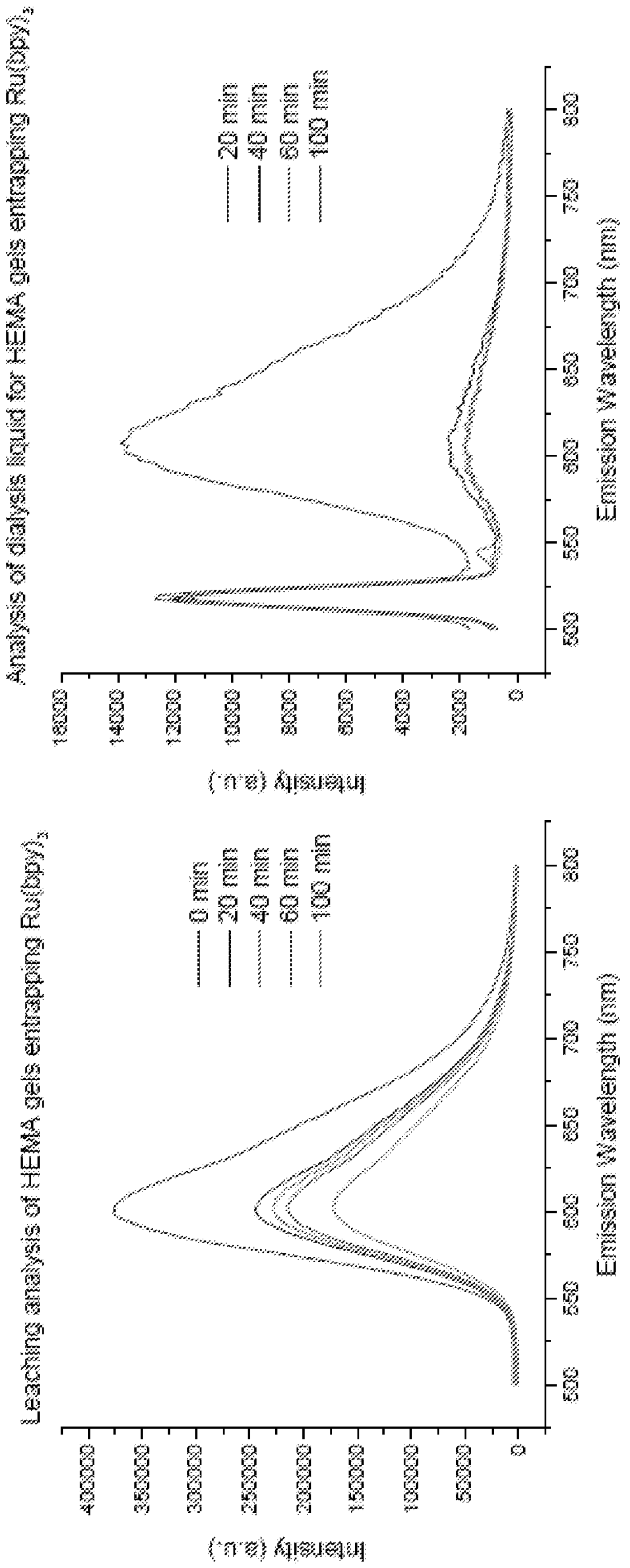
Figure 5:
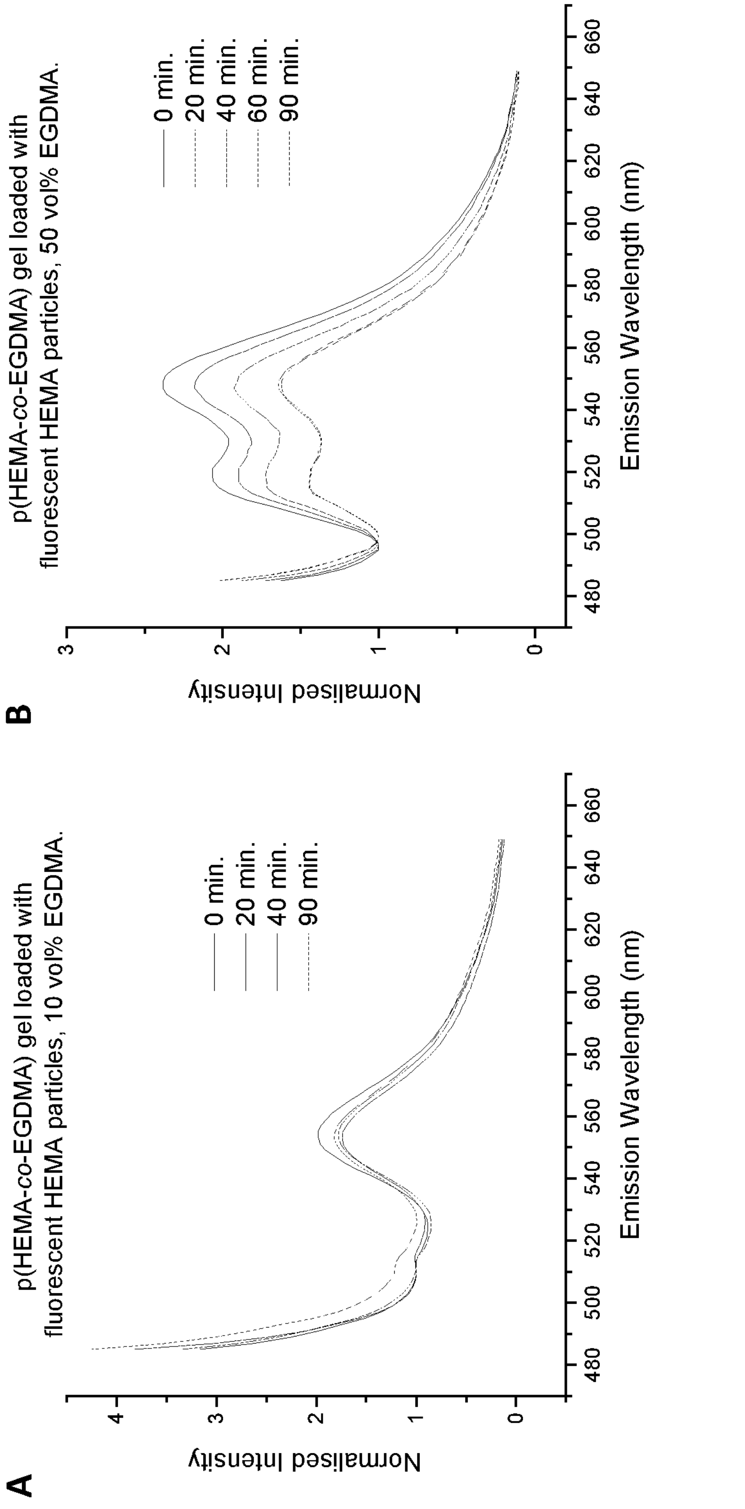
Figure 6:
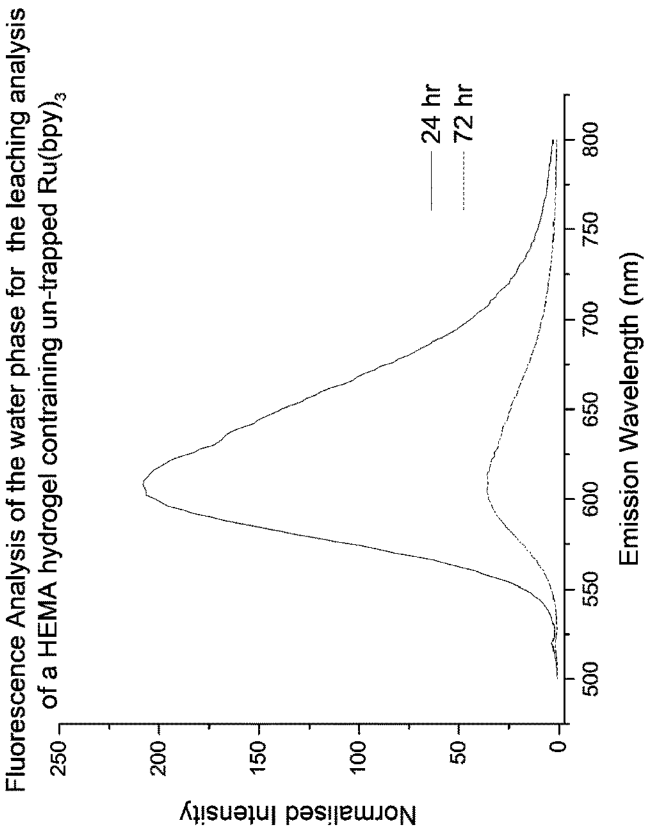
Figure 6:
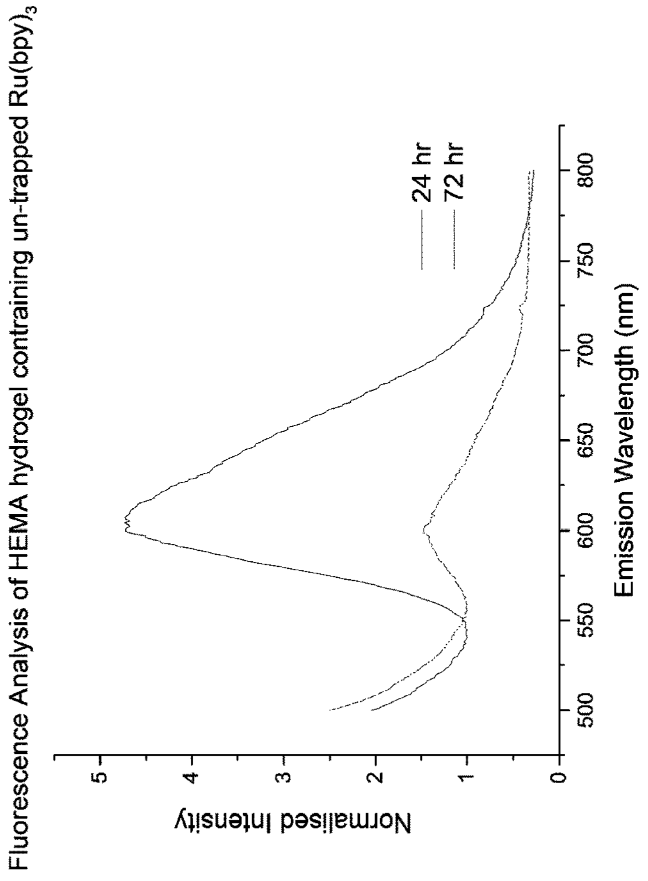
Figure 7:
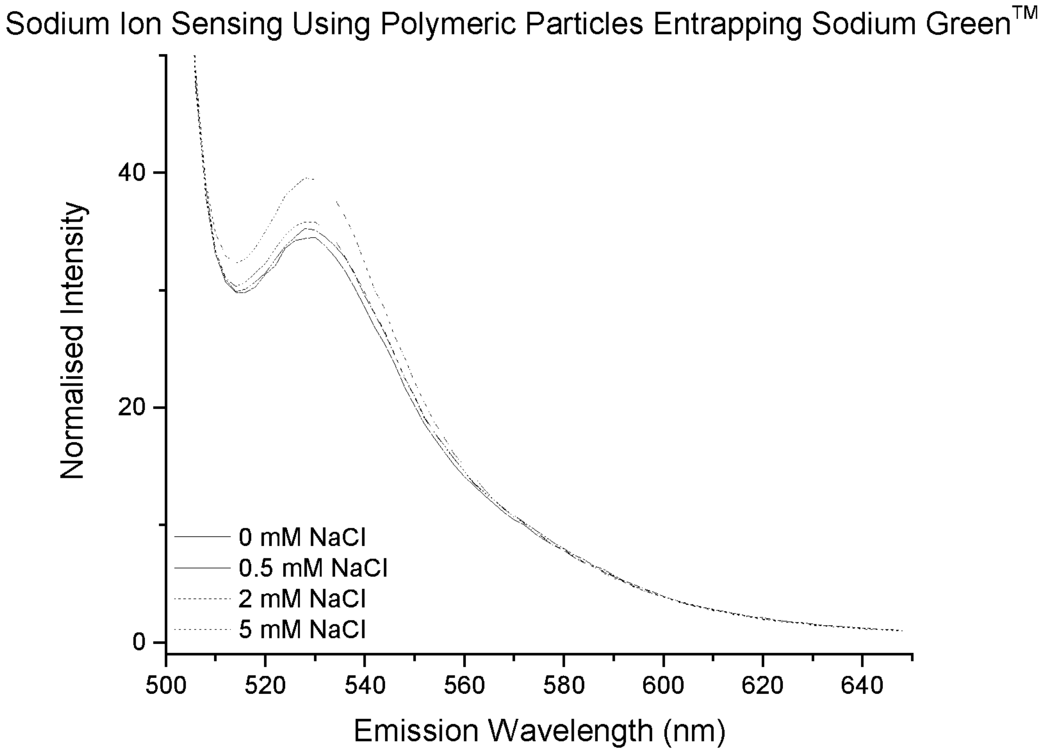

FIG. 4 short-term fluorescence leaching analysis of a HEMA hydrogel entrapping free $Ru(bpy)_3$ (not in particles) (left) and analysis of the water (right);

FIG. 5 shows fluorescence spectroscopy leaching analysis of fluorescent HEMA-shelled particles entrapped within p(HEMA-co-EGDMA) hydrogels of different crosslinking densities (as determined by monomer feed): 10 vol % (A) and 50 vol % (B) (λex=460 nm, measurements recorded every 2 nm, at integration time of 500 ms);

FIG. 6 shows fluorescence spectroscopy analysis for the long-term leaching of p(HEMA-co-EGDMA) hydrogels, crosslinked with 10 vol % EGDMA, entrapping non-particle Ru(bpy)3 (λex=440 nm, measurements recorded every 2 nm, at integration time of 500 ms); and FIG. 7 shows fluorescence spectroscopy sensing analysis for a p(HEMA-co-EGDMA) hydrogel entrapping Sodium Green™ encapsulated in HEMA-shelled particles, equilibrated in solutions of sodium chloride of differing concentrations, ($\lambda_{ex}$=488 nm, measurements recorded every 0.5 nm, at integration time of 500 ms).

EXAMPLES

Results and Discussion

Polymeric particles (polymeric "stars") were made encapsulating fluorophores. The polymeric particles were prepared by cross-linking an "outer" methacrylate monomer with an "inner" methacrylate monomer using a cross-linker.

Hydrogels were made with 10, 20 and 30 vol % crosslinking density, loaded with PEGMA and HEMA armed particles, with cores of both DEAEMA (pH responsive) and MMA (non-responsive).

Figure 1A:
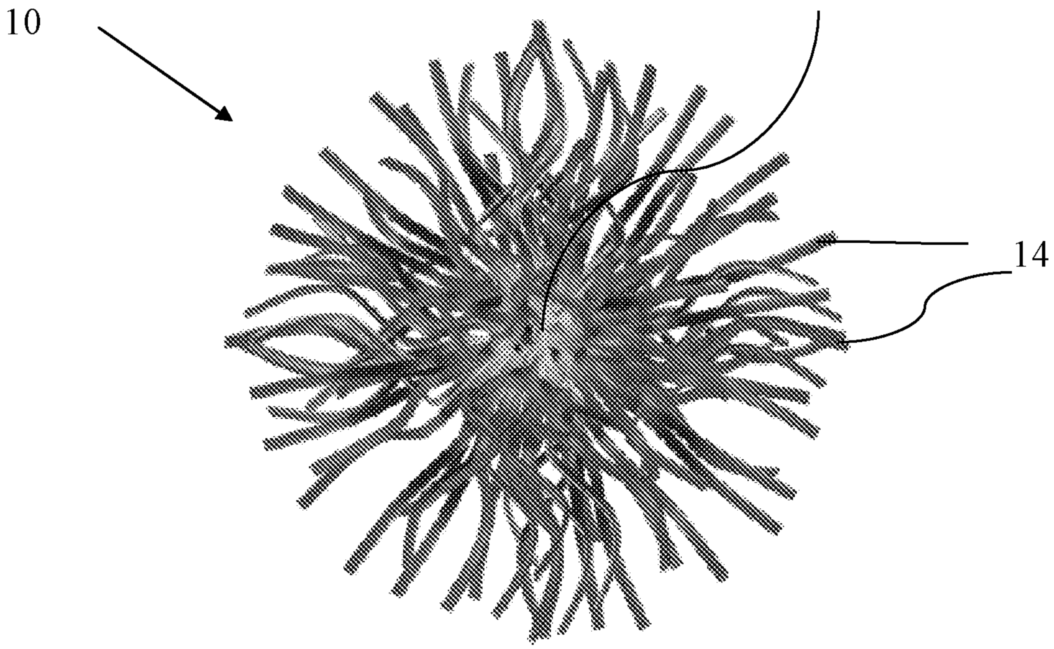
FIGS. 1A and 1B are schematic diagrams of a particle and a hydrogel in accordance with embodiments of the invention.
Figure 1B:
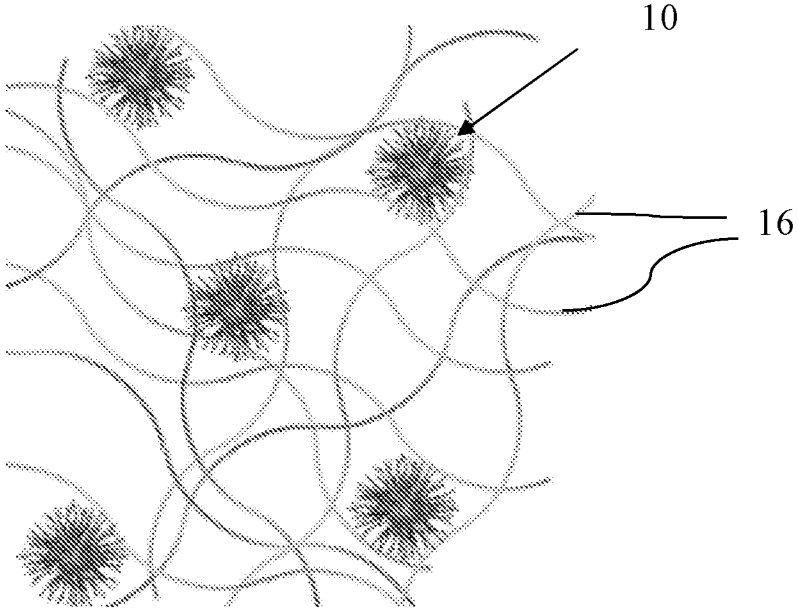
Figure 2:
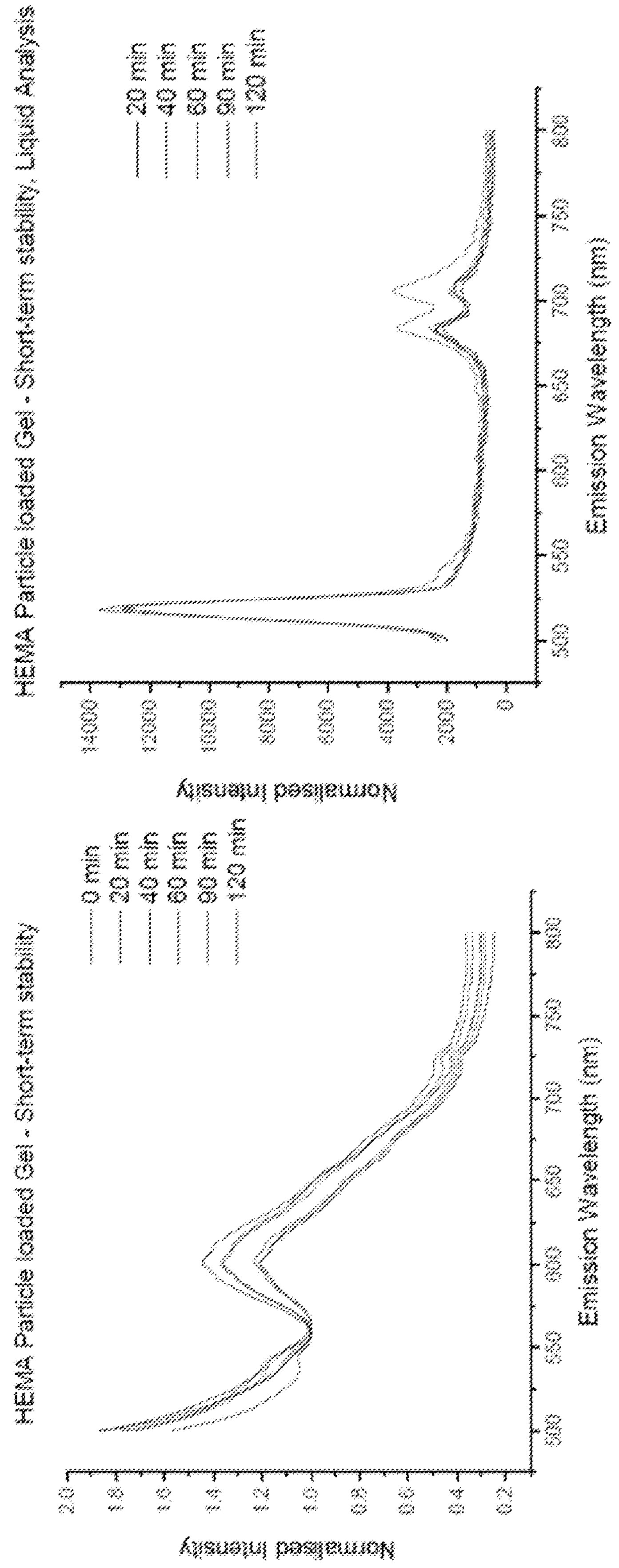
FIG. 2 shows short term fluorescence leaching analysis of a HEMA hydrogel loaded with HEMA armed $Ru(bpy)_3$ particles (left) and analysis of the water phase (right)

Leaching was prevented through the use of the "double entrapment" method, i.e. through the entrapment (encapsulation) of a fluorophore in particles and subsequent entrapment in the hydrogel. This is evidenced by FIG. 2, which shows a peak at λ=620 nm in the hydrogel and a lack of a peak at λ=620 nm in the solution analysis (the absorption maximum for the ruthenium complex), and a minimal decrease in the intensity of the gel fluorescence (with the slight decrease attributed to photobleaching).

Figure 3:
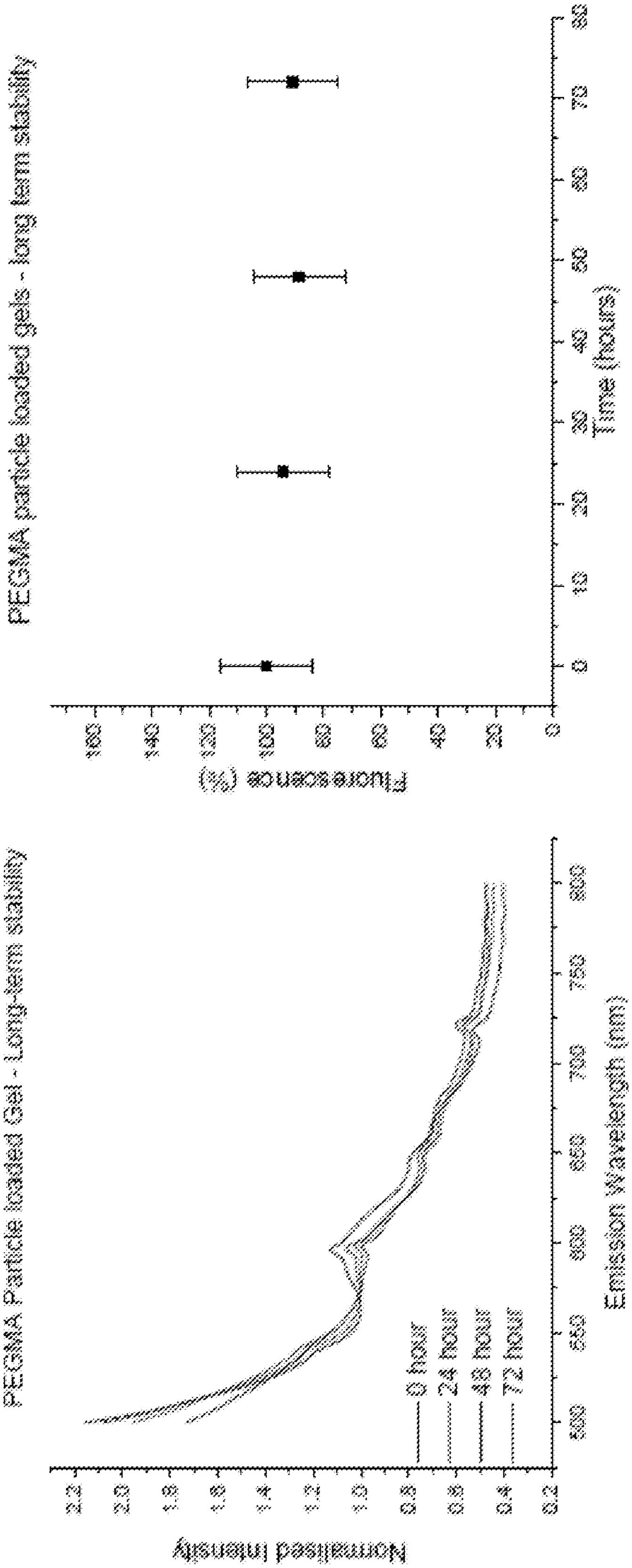
FIG. 3 shows long-term fluorescence leaching analysis of a HEMA hydrogel loaded with PEGMA particles (left) and the percentage fluorescence of the gel (right)

Long-term stability analysis indicated little/no leaching over the course of 4 days (FIG. 3).

In contrast a control (using hydrogels with non-particle trapped fluorophore) indicated significant leaching after 20 minutes, highlighting the improved stability of the complex in the hydrogel imparted by the encapsulation (FIG. 4). 0 minutes=uppermost line and 100 minutes=lowermost line.

Evaluation of different methods indicated the "secondary entrapment method" using a HEMA gel was the best method to prevent fluorophore leaching:

| | Method of entrapment | Decrease in fluorescence after 90 minutes (%) |
|---|---|---|
| Comp. Ex.1 | Trapping in a DMAm gel* | 94 |
| Comp. Ex. 2 | Trapping in a charged DMAEMA gel* | 64 |
| Ex.1 | Trapping in polymeric particles in a DMAm gel* | 40 |

-continued

| | Method of entrapment | Decrease in fluorescence after 90 minutes (%) |
|---|---|---|
| Comp. Ex.3 | Trapping in a HEMA gel# | 46 |
| Ex.3 | Trapping in polymeric particles in a HEMA gel# | 15 (±8)ł |

*fluorescein used as sensor,
#Ru(bpy)$_3$ used as sensor,
8% (±8%) over 72 hours.

łErrors generated though the measurement error calculated by 3 repeat measurements of a single gel within a cuvette.

Fluorescein Dimethacrylate

The polymeric particles were synthesised based on a modified literature procedure (Mabire, A. B., Brouard, Q., Pitto-Barry, A., Williams, R. J., Willcock, H., Kirby, N., Chapman, E., O'Reilly, R. K., Polym. Chem. 2016, 7, 5943). In order to attribute any leaching to the escape of polymeric particles from the hydrogel, fluorescein dimethacrylate was used to covalently attach the fluorophore into the polymeric particle. The inventors would prefer to avoid chemical bonding between the active material and the polymer chains, i.e. to ensure that the active material and the polymer chains remain separate entities, but this example provides a useful demonstrator model. It was hypothesised that any reduction in fluorescence intensity would therefore indicate leaching of the particles from the gel. The resultant HEMA-shelled or PEGMA-shelled polymeric particles were entrapped within a HEMA-based hydrogel, synthesised at both 10 vol % and 50 vol % crosslinking EGMDA.

Following polymerisation, hydrogels were dialysed in a beaker of distilled water for 24 hours prior to analysis. This step of pre-dialysis prior to analysis allows for removal of non-trapped particles and unreacted monomer, and was hypothesised to remove any effect of swelling on the fluorescence intensity recorded. Leaching analysis of the 10 vol % crosslinking EGDMA gels (A) and the 50 vol % crosslinking EGDMA gels (B) loaded with HEMA particles (500 μl of particle solution), using fluorescence spectroscopy, indicated significant retention of fluorophore over the 90 minutes, evident in a strong fluorescence intensity after 90 minutes (FIG. 5, A and B respectively, 0 minutes=uppermost line and 90 minutes=lowermost line). The presence of two peaks in the fluorescence spectrum of fluorescein has been demonstrated in the literature to be as a result of S1 to S0 transitions, with polymerisation shown to broaden the peaks.

Thermally Initiated Polymerisation

To ensure that entrapment of the particles within the hydrogel matrix using a thermally initiated method of polymerisation did not have a detrimental effect on the fluorescence of the probe, the fluorescence behaviour of the particles directly after synthesis, and after heating at 90° C. for 16 hours was evaluate. Results indicated that thermally initiated polymerisation did not impact on the fluorescence, with a slight increase in fluorescence intensity attributed to the slightly higher concentration of the heated sample owing to slight water evaporation during the heating.

Tris(Bipyridine) Ruthenium (II) Complex (Ru(Bpy)$_3$)

The fluorophore for development and optimisation of the demonstrator model was changed to tris(2,2'-bipyridyl)dichlororuthenium (II) complex, (Ru(bpy)$_3$). This fluorophore is significantly closer in structure, charge and hydrophilicity to the europium complexes described above. Whilst being metal centred, Ru(bpy)$_3$ is highly water soluble. Therefore, in preventing leaching of the Ru(bpy)$_3$ complex, it would be expected that the europium complex would not leach owing to its more amphipathic nature.

Owing to the significant effect of pH on the fluorescence intensity of the HEMA hydrogels when encapsulating fluorescent particles, Ru(bpy)$_3$-containing particles were synthesised with the permanently hydrophobic monomer methyl methacrylate (MMA) in place of the pH responsive DEAEMA. To ensure that the system was an accurate model, non-functionalised Ru(bpy)$_3$ was encapsulated within the polymeric particles without the use of chemical bonds.

Ru(bpy)$_3$ particles were incorporated into HEMA gels at different particle loadings and crosslinking densities achieved through varying the vol % of EGMDA and the volume of particle solution added to the hydrogel formulation prior to polymerisation, using the previously described method for the synthesis of p(HEMA-co-EGDMA) hydrogels.

| Gel | Crosslinking Density (vol % EGDMA) | Particle Loading (μL of particle solution, either HEMA or PEGMA shelled) |
|---|---|---|
| A | 10 | 50 |
| B | 10 | 100 |
| C | 10 | 250 |
| D | 25 | 50 |
| E | 25 | 100 |
| F | 25 | 250 |
| G | 50 | 50 |
| H | 50 | 100 |
| I | 50 | 250 |

Similarly to the previous leaching analysis, following polymerisation the gels were dialysed against deionised water for 24 hours prior to analysis, to ensure removal of unreacted monomer and non-trapped fluorescent particles. Analysis of the water phase of the leaching analysis for all of the gels, regardless of the particle loading or crosslinking density, indicated no fluorophore present in the solution over the course of analysis, with no peak at the emission maxima for Ru(bpy)$_3$ at $\lambda_{em}$=620 nm.

Moreover, no peak was present corresponding to the polymeric particles entrapping Ru(bpy)$_3$ at $\lambda_{em}$=608 nm, with the blue shift in emission between the free Ru(bpy)$_3$ and the entrapped Ru(bpy)$_3$ consistent with the literature. Moreover, visual analysis of the gels within the UV light box following the 90-minute leaching evaluation further confirmed with continued presence of red emission of the RU(II) complex from the fluorophore loaded particles within the hydrogel.

Using gels synthesised with 250 μl of particle solution and 10 vol % crosslinking EGMDA, the leaching analysis of HEMA-shelled and PEGMA-shelled Ru(bpy)$_3$ loaded particles entrapped within the HEMA gel were evaluated, for both short- and long-term stability. Analysis of the liquid phases for both studies indicated no loss of fluorophore from within the gel, with no peaks at the emission maximum for Ru(bpy)$_3$ ($\lambda_{em}$=620 nm) observed.

Moreover, analysis of the gels indicated significant retention of the Ru(bpy)$_3$ fluorophore over the course of two hours, with an overall decrease in fluorescence intensity of 40% and 24% for the HEMA-shelled and PEGMA-shelled particles, respectively. Additionally, the new cuvette method of analysis was demonstrated to produce more consistent results, without anomalous measurements of significantly higher, or lower/fluorescence intensities than the bulk of the fluorescence spectroscopy measurements during the study.

Repeating the leaching analysis over a longer period of time, through recording of the fluorescence intensity every 24 hours for a period of 3 days, allowed for evaluation of leaching over a time frame potentially applicable to longer-term continuous monitoring applications, for example waste water contamination monitoring. The long-term analysis indicated lower levels of leaching over the course of 72 hours, with a decrease in fluorescence intensity of 3% and 9% for the HEMA-shelled and PEGMA-shelled particles, respectively.

This lower degree of leaching over a longer period of analysis is attributed to less frequent water changes creating a lower concentration gradient therefore reducing leaching. Additionally, owing to more frequent measurements, the short-term leaching experiments may have a greater decrease in fluorescence intensity of the hydrogel over the course of the study owing to photobleaching. Regardless, these results strongly indicate minimal leaching of the fluorescent particles from the hydrogel over practically useful timescales.

To confirm that the secondary encapsulation method was indeed preventing leaching of the fluorophore from the gel, a control experiment was carried out using a HEMA-based hydrogel incorporating free (not encapsulated within particles) $Ru(bpy)_3$).

Leaching analysis on the resultant fluorescent gel clearly indicated significant loss of the fluorophore from the hydrogel over the period of 72 hours, with a large peak in the fluorescence spectrum attributable to the $Ru(bpy)_3$ at $\lambda_{em}$=610 nm clearly visible in the water phase after 24 and 72 hours (FIG. 6, 24 hours=upper line and 72 hours=lower line). Moreover, fluorescence spectroscopy analysis of the hydrogel indicates a decrease in fluorescence intensity of approximately 70% over the course of 72 hours, significantly greater than the 3% for the $Ru(bpy)_3$ when utilising the method of secondary encapsulation.

Sodium Green™

To allow for production of a demonstrator model with minimal leaching and the ability to sense ions, HEMA-shelled polymeric particles were synthesised entrapping the sodium ion-sensing fluorophore Sodium Green™. Particles were incorporated into HEMA-based hydrogels crosslinked with 10 vol % EGDMA, using the same synthetic procedure as previously described, and by the addition of 750 μl of particle solution to the hydrogel formulation.

To confirm a reduction in the leaching when using the method of secondary encapsulation of the fluorophore, the leaching behaviour of HEMA-based hydrogels loaded with Sodium Green™ encapsulated within the polymeric particles was also investigated. Repeating the same analysis procedure, as previously described, analysis indicated complete retention of the fluorophore over the course of 90 minutes, with no decrease in fluorescence intensity for the gel observed. Moreover, the fluorescence spectroscopy analysis of the water phase indicated the absence of Sodium Green™ in the solution, with no peak at its maximum emission wavelength in solution ($\lambda_{max}$=530 nm), and the absence of the Sodium Green™ loaded polymeric particles which have an emission maximum of $\lambda_{max}$=516 nm, with the blue shift in emission wavelength consistent with the literature. The absence of these peaks in the fluorescence spectrum of the water phases further confirm fluorescent particle retention in the hydrogel.

In order to again confirm that leaching is reduced owing to the secondary encapsulation of the Sodium Green™ within the polymeric particles, a control gel was synthesised using the previously described procedure, in which non-particle encapsulated, free Sodium Green™ was directly immobilised within the hydrogel.

Evaluation of the leaching behaviour of the Sodium Green™ incorporating hydrogels (through either secondary encapsulation or direct entrapment within the hydrogel) was carried out as previously. Analysis of the HEMA-based hydrogels entrapping non-particle Sodium Green™ indicated significant leaching of the fluorophore from within the gel after only 20 minutes, and a decrease in fluorescence intensity of 60% over the course of the 90 minutes, and with the loss of the fluorophore from within the gel confirmed by its presence within the water phase of the leaching analysis set-up.

Having successfully demonstrated that the method of secondary encapsulation prevents leaching of the sodium-responsive fluorophore, attention was directed to confirming the sensing ability of the encapsulated fluorophore. Initial studies were carried out using the solution of Sodium Green™ HEMA-shelled polymeric particles. Fluorescence spectroscopy analysis confirmed a slight increase in fluorescence intensity as the concentration of sodium ions added increased (FIG. 7, 5 mM NaCl=uppermost line and 0=lowermost line), confirming that encapsulation of the fluorophore has not impacted on the ability of the luminescent sensor to function (a commonly reported problem in other sensing materials).

CONCLUSION

There is provided a system in which there is relatively little leaching of the ion-responsive fluorophore from within a hydrogel matrix over a clinically relevant timescale. Moreover, the range of fluorophores (metal and non-metal centred) and the different monomers used in the production of the hydrogels and particles indicate the potential scope of producing a universally applicable system for fluorophore entrapment for sensing applications. Moreover, we have been able to successfully entrap an ion-sensing fluorophore within a polymeric particle, and confirm that entrapment does not prevent the ion-sensing of the fluorophore.

Whilst this project has mainly focussed on the development of a demonstrator model capable of sodium sensing, incorporation of other responsive sensors could produce systems with relevance to clinical diagnostics, medical devices, biosensors and other applications.

Methodology

Materials

The following reagents were used as received: Fluorescein sodium salt (BioReagent, Sigma-Aldrich), ethylene glycol dimethacrylate (EGDMA, 98%, Sigma-Aldrich), poly(ethylene glycol) methylether methacrylate (PEGMA, $M_n$—300 g/mol), 2-(diethylamino)ethyl methacrylate (DEAEMA, 99%, Sigma-Aldrich), potassium persulfate (KPS, >99%, Sigma-Aldrich), Sodium Green™ (Fisher Scientific), sodium chloride (NaCl, >98%, Sigma-Aldrich), methyl methacrylate (MMA, 99%, Sigma-Aldrich), 2-hydroxyethyl methacrylate (HEMA, 97%, Sigma-Aldrich) and Tris(2,2'-bipyridyl)dichlororuthenium complex ($Ru(bpy)_3$, 99.95%, Sigma-Aldrich). Inhibitor for all monomers was removed by passing through a plug of basic alumina. DMSO was used as received from Sigma-Aldrich. Silicone Isolators were received from Grace Bio-Labs and the plastic layers removed.

| Abbreviation | Name | CAS |
|---|---|---|
| HEMA | 2-hydroxyethyl methacrylate | 868-77-9 |
| PEGMA (Mn – 300 Da) | Poly(ethylene glycol) methyl ether methacrylate | 26915-72-0 |
| DEAEMA | 2-(diethylamino) ethyl methacrylate | 105-16-8 |
| MMA | Methyl methacrylate | 80-60-6 |
| EGDMA | Ethylene glycol dimethacrylate | 97-90-5 |
| $Ru(bpy)_3$ | Tris(2,2'-bipyridyl)dichlororuthenium (II) hexahydrate | 50525-27-4 |
| Fluorescein (sodium salt) | Fluorescein sodium salt | 518-47-8 |
| Sodium Green | Sodium Green, cell impermeant | — |
| Eu-complex | $[Eu.L^{l}]^{+}$ (Chem. Commun., 2015, 51, 10879) | — |
| DMAm | N,N-dimethylacrylamide | 2680-03-7 |
| HPMA | 2-hydroxypropyl methacrylamide | 21442-01-3 |
| DMAEMA | 2-(dimethylamino)ethyl methacrylate | 2867-47-2 |
| BuMA | Butyl methacrylate | 97-88-1 |
| GlyMA | Glycidyl methacrylate | 106-91-2 |
| Glycerol methacrylate | Glycerol monomethacrylate | 5919-74-7 |

Instrumentation

Fluorescence spectroscopy measurements were carried out using a Fluoromax fluorometer. For fluorescein sodium salt: λex=460 nm, λem=490-620 nm, for Sodium Green™: λex=488 nm, λem=500-625 nm, for fluorescein dimethacrylate: λex=460 nm, λem=490-620 nm; and for $Ru(bpy)_3$: λex=440 nm, λem=500-800 nm. For leaching studies, measurements were recorded at 2 nm intervals, with an integration time of 500 ms. For all other analyses, measurements were recorded at 0.5 nm intervals, with an integration time of 500 ms. Silicone isolators were used to produce hydrogels of uniform sizes, with the isolator placed between 2 slides, with a 2 mm gap between the top of the isolator and the top covering slide to allow for injection of the reaction solution (425 μl). Following curing, the top slide was removed, the gel removed from the slide and dialysed against deionised water to remove unreacted monomer and un-trapped fluorophore.

Synthetic Methods

Synthesis of Polymeric Particles:

PEGMA Armed Particles with Covalently Attached Fluorescein (Large Particles, pH Responsive, Non-Ion-Sensing)

PEGMA ($M_n$—300 g/mol, 42 μL) was first dissolved in 50 mL deionised water; EGDMA (26 μL), fluorescein dimethacrylate (14 mg) and DEAEMA (2.75 mL) were added to the stirring solution. Whilst stirring (490 RPM), the mixture was heated to 65° C. and purged with nitrogen gas for 30 minutes. Separately, the initiator potassium persulfate (0.025 g) was dissolved in water (1 mL) and degassed with nitrogen, prior to addition to the reaction mixture. The solution was stirred at 65° C. for 16 hours under a nitrogen atmosphere. The resultant particles were purified by exhaustive dialysis (MWCO 3.5 kDa) against deionised water.

HEMA Armed Particles with Covalently Attached Fluorescein (Large Particles, pH Responsive, Non-Ion-Sensing)

HEMA (100 μL) was first dissolved in 50 mL deionised water; EGDMA (26 μL), fluorescein dimethacrylate (14 mg) and DEAEMA (2.75 mL) were added to the stirring solution. Whilst stirring (490 RPM), the mixture was heated to 65° C. and purged with nitrogen gas for 30 minutes. Separately, the initiator potassium persulfate (0.025 g) was dissolved in water (1 mL) and degassed with nitrogen, prior to addition to the reaction mixture. The solution was stirred at 65° C. for 16 hours under a nitrogen atmosphere. The resultant particles were purified by exhaustive dialysis (MWCO 3.5 kDa) against deionised water.

PEGMA Armed Particles Loaded with $Ru(Bpy)_3$ (Large Particles, Non-Responsive, Non-Ion-Sensing)

PEGMA ($M_n$—300 g/mol, 42 μL) was first dissolved in 50 mL deionised water; EGDMA (52 μL), MMA (1.5 mL), and $Ru(bpy)_3$ (2 mg) were added to the stirring solution. Whilst stirring (490 RPM), the mixture was heated to 65° C. and purged with nitrogen gas for 30 minutes. Separately, the initiator potassium persulfate (0.025 g) was dissolved in water (1 mL) and degassed with nitrogen, prior to addition to the reaction mixture. The solution was stirred at 65° C. for 16 hours under a nitrogen atmosphere. The resultant particles were purified by exhaustive dialysis (MWCO 3.5 kDa) against deionised water.

HEMA Armed Particles Loaded with $Ru(Bpy)_3$ (Large Particles, Non-Responsive, Non-Ion-Sensing)

HEMA (100 μL) was first dissolved in 50 mL deionised water; EGDMA (52 μL), MMA (1.5 mL), and $Ru(bpy)_3$ (2 mg) were added to the stirring solution. Whilst stirring (490 RPM), the mixture was heated to 65° C. and purged with nitrogen gas for 30 minutes. Separately, the initiator potassium persulfate (0.025 g) was dissolved in water (1 mL) and degassed with nitrogen, prior to addition to the reaction mixture. The solution was stirred at 65° C. for 16 hours under a nitrogen atmosphere. The resultant particles were purified by exhaustive dialysis (MWCO 3.5 kDa) against deionised water.

HEMA Armed Particles Loaded with Sodium Green™ (Large Particles, Non-Responsive, Ion-Sensing)

HEMA (100 μL) was first dissolved in 50 mL deionised water; EGDMA (52 μL), MMA (1.5 mL), and Sodium Green™ (500 μl of 60 μM solution made up in DMSO) were added to the stirring solution. Whilst stirring (490 RPM), the mixture was heated to 65° C. and purged with nitrogen gas for 30 minutes. Separately, the initiator potassium persulfate (0.025 g) was dissolved in water (1 mL) and degassed with nitrogen, prior to addition to the reaction mixture. The solution was stirred at 65° C. for 16 hours under a nitrogen atmosphere. The resultant particles were purified by exhaustive dialysis (MWCO 3.5 kDa) against deionised water.

Hydrogel Synthesis:

Please note, in the following methods, hydrogels are immediately removed from the silicone mould when still hot. If the gels are allowed to cool within the silicon mould and sandwiched between the two glass slides it is very difficult to remove the gels from the slides without cracking the gel. If immediate removal is not possible and the gel has cooled and is now hard/brittle, submerge the entire silicone mould and glass slide set up in a petri dish filled with distilled water. Check periodically to ensure that the gel is hydrating. Once hydrated remove the gel from within the silicone moulds and glass slides, and continue with the re-dialysis step.

Typical Procedure for the Synthesis of p(DMAm-Co-MBAc) Hydrogels Loaded with Fluorescein Sodium Salt (Comparative Example 1).

DMAm (0.6 g, 1 eq.), MBAc (2 wt %) and Irgacure 184 (0.1 wt %) were dissolved in a solution of fluorescein sodium salt (100 μM in deionised water, 5 mL). Following purging with nitrogen, 100 μL of reaction solution was placed into the silicone mould and the mixture cured for 90 minutes.

Typical Procedure for the Synthesis of p(DMAm-Co-EGDMA) Hydrogels Loaded with Fluorescein Sodium Salt (Comparative Example 2).

DMAm (0.6 g, 1 eq.), EGDMA (2 wt %) and Irgacure 184 (0.1 wt %) were dissolved in a solution of fluorescein sodium salt (100 μM in deionised water, 5 mL). Following purging with nitrogen, 100 μL of reaction solution was placed into the silicone mould and the mixture cured for 90 minutes.

Typical Procedure for the Synthesis of p(DEAEMA-Co-EGDMA-Co-PEGMA) Polymeric Stars Loaded with Fluorescein Sodium Salt.

PEGMA (42 μL, 1 eq.) was first dissolved in 50 mL deionised water, stirred for 2 minutes, and EGDMA (2 wt %) and DEAEMA (10 wt %) were added to the solution. The mixture, whilst stirred, was degassed by purging with nitrogen for 30 minutes, and further heated at 65° C. whilst purging was continued. The initiator (KPS, 0.1 wt %) was dissolved separately in water (1 mL) and the solution purged with nitrogen before being added to the reaction mixture. The reaction was stirred at 65° C. for 16 hours and cooled to room temperature. The particles were purified by exhaustive dialysis (MWCO=3.5 kDa) against deionised water.

Typical Procedure for the Synthesis of a HEMA Hydrogel Loaded with Fluorescent PEGMA-Fluorescein Particles (10 Vol % Crosslinking EGDMA)

AIBN (0.002 g) was dissolved in a solution of HEMA (0.9 mL) and EGDMA (0.1 mL). Fluorescein dimethacrylate-PEGMA shelled particles (250 μl of particle solution) were added and the solution purged with nitrogen for 20 minutes. The solution (425 μl) was placed into the silicone mould and the mixture cured in the oven at 85° C. for 3 hours. Whilst still warm, the slides were removed from the oven, the gel removed from the silicone mould and dialysed in water for 24 hours.

Typical Procedure for the Synthesis of a HEMA Hydrogel Loaded with Fluorescent HEMA-Fluorescein Particles (10 Vol % Crosslinking EGDMA)

AIBN (0.002 g) was dissolved in a solution of HEMA (0.9 mL) and EGDMA (0.1 mL). Fluorescein dimethacrylate-HEMA shelled particles (250 μl of particle solution) were added and the solution purged with nitrogen for 20 minutes. The solution (425 μl) was placed into the silicone mould and the mixture cured in the oven at 85° C. for 3 hours. Whilst still warm, the slides were removed from the oven, the gel removed from the silicone mould and dialysed in water for 24 hours.

Typical Procedure for the Synthesis of a HEMA Hydrogel Loaded with Fluorescent PEGMA-Ru(Bpy)$_3$ Particles (10 Vol % Crosslinking EGDMA)

AIBN (0.002 g) was dissolved in a solution of HEMA (0.9 mL) and EGDMA (0.1 mL). PEGMA shelled Ru(bpy)$_3$ entrapping polymeric particles (250 μl of particle solution) were added and the solution purged with nitrogen for 20 minutes. The solution (425 μl) was placed into the silicone mould and the mixture cured in the oven at 85° C. for 3 hours. Whilst still warm, the slides were removed from the oven, the gel removed from the silicone mould and dialysed in water for 24 hours.

Typical Procedure for the Synthesis of a HEMA Hydrogel Loaded with Fluorescent HEMA-Ru(Bpy)$_3$ Particles (10 Vol % Crosslinking EGDMA)

AIBN (0.002 g) was dissolved in a solution of HEMA (0.9 mL) and EGDMA (0.1 mL). HEMA shelled Ru(bpy)$_3$ entrapping polymeric particles (250 μl of particle solution) were added and the solution purged with nitrogen for 20 minutes. The solution (425 μl) was placed into the silicone mould and the mixture cured in the oven at 85° C. for 3 hours. Whilst still warm, the slides were removed from the oven, the gel removed from the silicone mould and dialysed in water for 24 hours.

Typical Procedure for the Synthesis of a HEMA Hydrogel Loaded with Fluorescent Ru(Bpy)$_3$ (10 Vol % Crosslinking EGDMA)

AIBN (0.002 g) was dissolved in a solution of HEMA (0.9 mL) and EGDMA (0.1 mL). Ru(bpy)$_3$ (500 μl of 60 μM solution made up in water) was added and the solution purged with nitrogen for 20 minutes. The solution (425 μl) was placed into the silicone mould and the mixture cured in the oven at 85° C. for 3 hours. Whilst still warm, the slides were removed from the oven, the gel removed from the silicone mould and dialysed in water for 24 hours.

Typical Procedure for the Synthesis of a HEMA Hydrogel Loaded with Fluorescent HEMA-Sodium Green™ Particles (10 Vol % Crosslinking EGDMA)

AIBN (0.002 g) was dissolved in a solution of HEMA (0.9 mL) and EGDMA (0.1 mL). HEMA shelled Sodium Green™ entrapping polymeric particles (250 μl of particle solution) were added and the solution purged with nitrogen for 20 minutes. The solution (425 μl) was placed into the silicone mould and the mixture cured in the oven at 85° C. for 3 hours. Whilst still warm, the slides were removed from the oven, the gel removed from the silicone mould and dialysed in water for 24 hours.

Typical Procedure for the Synthesis of a HEMA Hydrogel Loaded with Fluorescent Sodium Green™ (10 Vol % Crosslinking EGDMA)

AIBN (0.002 g) was dissolved in a solution of HEMA (0.9 mL) and EGDMA (0.1 mL). Sodium Green™ (500 μl of 60 μM solution made up in DMSO) was added and the solution purged with nitrogen for 20 minutes. The solution (425 μl) was placed into the silicone mould and the mixture cured in the oven at 85° C. for 3 hours. Whilst still warm, the slides were removed from the oven, the gel removed from the silicone mould and dialysed in water for 24 hours.

The invention claimed is:

1. A hydrogel comprising a particle physically entrapped within a hydrogel matrix, wherein:

the particle comprises an active material and a first polymeric material, wherein:

the first polymeric material is a cross-linked co-polymer formed from:

(a) a C1-C12 alkyl methacrylate or a C1-C12 alkyl acrylate, and (b) a heteroalkyl methacrylate or a heteroalkyl acrylate, wherein the heteroatom or each heteroatom in the heteroalkyl groups is O, such that the first polymeric material has a plurality of chains, wherein each of the chains of the first polymeric material has a first end and a second end, wherein the active material and the first ends of the chains form a core;

the second ends of the chains extend outwardly away from the core to form a shell;

the active material is retained within the core of the particle by hydrophobic interactions and/or hydrophilic interactions;

the active material is not covalently attached to the chains; and the active material comprises a metal complex, wherein the metal complex comprises a metal selected from copper, ruthenium, zinc, iridium, europium, terbium, gadolinium, and ytterbium; and the hydrogel matrix comprises a crosslinked polymethacrylate or a crosslinked polyacrylate, such that the active material is firstly encapsulated within the particle and secondly encapsulated within the hydrogel, so as to prevent leaching of the active material from the hydrogel.

2. The hydrogel of claim 1, wherein the particle has a diameter of 50 to 1000 nm when measured in solution by dynamic light scattering.

3. A method for the preparation of a hydrogel, the method comprising providing a particle comprising an active material and a first polymeric material, wherein the first polymeric material is a crosslinked co-polymer formed from:

(a) a C1-C12 alkyl methacrylate or a C1-C12 alkyl acrylate, and (b) a heteroalkyl methacrylate or a heteroalkyl acrylate, wherein the heteroatom or each heteroatom in the heteroalkyl groups is O, such that the first polymeric material has a plurality of chains, wherein each of the chains of the first polymeric material have a first end and a second end, wherein the active material and the first ends of the chains form a core;

the second ends of the chains extend outwardly away from the core to form a shell;

the active material is retained within the core of the particle by hydrophobic interactions and/or hydrophilic interactions;

the active material is not covalently attached to the chains;

wherein the active material comprises a metal complex, wherein the metal complex comprises a metal selected from copper, ruthenium, zinc, iridium, europium, terbium, gadolinium, and ytterbium; and cross-linking a methacrylate monomer or an acrylate monomer in the presence of the particle to produce a hydrogel matrix having the particle physically entrapped in the hydrogel matrix, so as to prevent leaching of the active material from the hydrogel.

4. The method of claim 3, comprising an initial step, before cross-linking of the methacrylate monomer or the acrylate monomer, of preparing the particle from the active material, a C1-C12 alkyl methacrylate or a C1-C12 alkyl acrylate, and a heteroalkyl methacrylate or a heteroalkyl acrylate, wherein the heteroatom or each heteroatom in the heteroalkyl groups is O.

5. The method of claim 4, wherein preparing the particle comprises purification.

6. A method for measuring the concentration of a chemical species in a sample, the method comprising:

contacting the sample with the hydrogel of claim 1;

measuring a change in an optical property of the active material produced by contacting the sample with the active material; and converting said change in optical property to said concentration.

7. The method of claim 6, wherein the sample is an aqueous sample.

8. The method of claim 6, wherein the chemical species is a nucleoside polyphosphate (NPP) anion.

9. The hydrogel of claim 1, wherein the metal is selected from europium, terbium, gadolinium, and ytterbium.

10. The hydrogel of claim 1, wherein the metal complex is a Eu(III) complex.

11. The hydrogel of claim 10, wherein the Eu(III) complex has the structure:

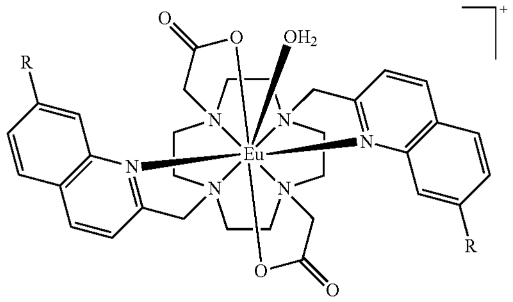

wherein each R is independently selected from hydrogen, C1-C12 alkyl, and $NHCOR^1$, where $R^1$ is H or C1-C12 alkyl.

12. The hydrogel of claim 1, wherein:

the C1-C12 alkyl methacrylate or C1-C12 alkyl acrylate is methyl methacrylate, the heteroalkyl methacrylate or heteroalkyl acrylate is 2-hydroxyethyl methacrylate or poly(ethylene glycol) methyl ether methacrylate, and the crosslinked polymethacrylate or polyacrylate is crosslinked 2-hydroxyethyl methacrylate.

* * * * *